(12) United States Patent
Belter

(10) Patent No.: US 9,242,942 B2
(45) Date of Patent: Jan. 26, 2016

(54) PURIFICATION OF ARYLTRIAZOLES

(71) Applicant: Randolph K Belter, Zachary, LA (US)

(72) Inventor: Randolph K Belter, Zachary, LA (US)

( * ) Notice: Subject to any disclaimer, the term of this patent is extended or adjusted under 35 U.S.C. 154(b) by 0 days.

(21) Appl. No.: 13/932,829

(22) Filed: Jul. 1, 2013

(65) Prior Publication Data

US 2015/0005508 A1    Jan. 1, 2015

(51) Int. Cl.
*C07D 249/18* (2006.01)

(52) U.S. Cl.
CPC ..................... *C07D 249/18* (2013.01)

(58) Field of Classification Search
CPC ...................................... C07D 249/06
USPC .............................. 548/257, 262.4
See application file for complete search history.

(56) References Cited

U.S. PATENT DOCUMENTS

| | | | |
|---|---|---|---|
| 2,861,078 A | 11/1958 | Miller et al. | |
| 3,227,726 A | 1/1966 | Levy | |
| 3,334,054 A | 8/1967 | Howard et al. | |
| 3,564,001 A | 2/1971 | Long | |
| 3,637,514 A | 1/1972 | Spatz et al. | |
| 3,639,431 A | 2/1972 | McTeer et al. | |
| 3,732,239 A | 5/1973 | Spatz et al. | |
| 3,970,667 A | 7/1976 | Gengnagel et al. | |
| 4,158,660 A | 6/1979 | Gavin et al. | |
| 4,170,521 A | 10/1979 | Carr | |
| 4,269,987 A | 5/1981 | Carr et al. | |
| 4,299,965 A | 11/1981 | Chan et al. | |
| 4,363,914 A | 12/1982 | Long et al. | |
| 4,424,360 A | 1/1984 | Hagedorn et al. | |
| 4,528,381 A | 7/1985 | Gencarelli et al. | |
| 4,549,026 A | 10/1985 | Deur et al. | |
| 4,918,195 A | 4/1990 | Schnegg et al. | |
| 5,914,409 A | 6/1999 | Adkins et al. | |

OTHER PUBLICATIONS

IUPAC. Compendium of Chemical Terminology, 2nd ed. (the "Gold Book"). Compiled by A. D. McNaught and A. Wilkinson. Blackwell Scientific Publications, Oxford (1997). XML on-line corrected version: http://goldbook.iupac.org (2006-) created by M. Nic, J. Jirat, B. Kosata; updates compiled by A. Jenkins. ISBN 0-9678550-9-8. doi:10.1351/goldbook.*

* cited by examiner

*Primary Examiner* — Michael Barker
*Assistant Examiner* — Karen Cheng

(57) ABSTRACT

Impure aryltriazoles such as benzotriazole and tolyltriazole that are contaminated with dark colored imputities can be purified by conversion to an aryltriazole acid salt by treatment with aqueous acid. The aryltriazole acid salt is water soluble whereas the dark colored impurities are not. The aryltriazole acid salt solution is separated from the dark colored impurities and the aryltriazole is recovered by neutralization with base.

24 Claims, No Drawings

PURIFICATION OF ARYLTRIAZOLES

FIELD OF INVENTION

This invention relates to an improved process for preparing lightly colored or colorless aryltriazoles. Aqueous solutions of the anions of said aryltriazoles are, in addition, clear and free of fine particulate matter. The color improvement of this process occurs when impure aryltriazoles are solubilized in acidic solution and separated in the liquid phase from dark, insoluble impurities. The process of the present invention greatly reduces or eliminates the need for filtration, color adsorption or distillation.

BACKGROUND OF THE INVENTION

The first reference to the preparation of aryltriazoles is *Berichte* 9, 219 (1876) in which benzotriazoles and tolyltriazoles were prepared. In describing this process for purifying aryltriazoles, we specifically include benzotriazole, tolyltriazole and alkyl-substituted analogs of both. The term tolyltriazole is meant to mean 4-methylbenzotriazole, 5-methylbenzotriazole and mixtures of the two. Non-proprietary processes for the preparation of aryltriazoles were subsequently published in *Ber. Chem.* 33, 261 (1900), *Gazz. Chim. Ital.* 51, 267 (1921), *J. Chem. Soc.* 954 (1926), *J. Am. Chem. Soc.* 57, 1835 (1935), *Organic Synthesis* 20, 16 (1940), and *Chem. Berichte* 100, 1646 (1967). Proprietary references to the preparation of aryltriazoles are U.S. Pat. No. 2,861,078 (1958), U.S. Pat. No. 3,227,726 (1966), U.S. Pat. No. 3,637,514 (1972), DT2,351,595 (1973), U.S. Pat. No. 3,732,239 (1973), JP51-65760 (1976), U.S. Pat. No. 4,158,660 (1979), GB1,581,407 (1980), U.S. Pat. No. 4,299,965 (1981), U.S. Pat. No. 4,363,914 (1982), U.S. Pat. No. 4,424,360 (1984), U.S. Pat. No. 4,528,381 (1985), U.S. Pat. No. 4,549,026 (1985), and U.S. Pat. No. 5,914,409 (1999).

Generally, these methods of preparation produce an aryltriazole product that is darkened and discolored by various impurities. Some processes even produce aryltriazole products that are black. The free aryltriazole, that is an aryltriazole that is not in its anionic form, is insoluble in aqueous solutions and is often isolated from aqueous solutions as a solid or a melt. Such solids or melts usually contain most of the colorizing impurities initially in the aqueous solution. Such impurities are typically generated during the reaction processes that convert o-aryldiamines to aryltriazoles. Such impurities may also be introduced into the product aryltriazoles as impurities in the o-aryldiamine starting materials. The dark and colored impurities have been described variously as "colored-bodies" or "tars". The exact nature of the colored impurities has been long conjectured, and likely include monoarylamines, monoaryldiazonium compounds, dimers of meta-aryldiamines, etc. The exact nature is of little consequence as the colored impurity bulk likely consists of many or all these components. References to the purification of aryltriazoles are U.S. Pat. No. 3,334,054 (1967), U.S. Pat. No. 3,564,001 (1971), U.S. Pat. No. 3,639,431 (1972), U.S. Pat. No. 3,970,667 (1976), U.S. Pat. No. 4,170,521 (1979), U.S. Pat. No. 4,269,987 (1981), JP 56-016478 (1981), U.S. Pat. No. 4,269,987 (1981), EP0303772 (1988), U.S. Pat. No. 4,918,195 (1990), JP04-360879 (1992), CN1,821,232 (2006), and JP224,014 (2007).

Specific methods of purification that have been disclosed include various distillation methodologies. Of consequence is that the colored impurities exhibit very similar boiling points, making separation by distillation difficult. Some components of the colored impurities boil at slightly lower temperatures than the target aryltriazoles while the remainder boil at higher temperatures, making fractionation necessary. Some components of the colored impurities may actually azeotrope with the target aryltriazole, making complete separation by a single distillation impossible. Also, colored impurities may entrain with the distillate stream, carrying droplets of higher boiling colored impurity to the overheads and contaminating the final product. Generally, because of the high boiling point of the aryltriazoles, high-vacuum distillation is necessary to prevent decomposition of the aryltriazole and to keep temperatures within safe ranges. In some cases, additives or special conditions are used. U.S. Pat. No. 4,918,195 and EP0308772 teach that distillation from basic compounds, i.e. NaOH, reduces the color of the distillate to a yellow which over time changes to grey. Similarly, U.S. Pat. No. 4,170,521 discloses the distillation of aryltriazoles from formaldehyde to generate benzotriazole and tolyltriazole of reduced color. In some cases, the aryltriazole is co-distilled or azeotroped with another compound to ease the distillation and improve yield. For example, U.S. Pat. No. 3,639,431 discloses the co-distillion of benzotriazole with polyethylene glycols. The distillate is an aryltriazole/polyethylene glycol mixture intended to be marketed as the mixture. Distillation has the disadvantage of needing expensive equipment. Another disadvantage is the concentration of high energy by-products in the still bottoms and the accompanying safety risks.

Another method of purification of aryltriazoles from colored impurities is adsorbance onto decolorizing media. Activated carbon, kieselguhr, diatomacious earth, clays, alumina, fuller's earth, pumice and sodium dithionite may be used to remove colored impurities from solutions of aryltriazoles. In many cases, the aryltriazole was in the anionic form, or was converted into the anionic form through the action of base, commonly hydroxide. For example, U.S. Pat. No. 3,970,667 discloses the use of active carbon, kieselguhr and then sodium dithionite sequentially to purify a sodium tolyltriazole solution. Once the anionic form of the aryltriazole is sufficiently purified, it is generally recovered by acidifying the solution to a pH of about 5 or 6 wherein the free aryltriazole is regenerated and separates from solution as the solid or melt, depending on temperature. U.S. Pat. No. 3,334,054 discloses a decolorization process in glycol solutions rather than aqueous solutions. JP04-360879 discloses performing the decolorization first under basic (alkaline) conditions, then repeats under acidic conditions before neutralizing and isolating the product. Unfortunately, the aryltriazole is also adsorbed onto the decolorizing media to some extent. As large quantities of decolorizing media are generally required to obtain acceptably purified aryltriazole, losses of aryltriazole to adsorption onto the media are appreciable. Also, large quantities of adsorbant must be used and subsequently disposed. In U.S. Pat. No. 3,970,667, 75 weight percent carbon plus 10 weight percent kieselguhr plus 10 weight percent sodium dithionite is used to effect decolorization. All these decolorization processes have the distinct disadvantage of handling solid decolorizing reagent, making addition and removal cumbersome.

Another method of purification of aryltriazoles from colored impurities is crystallization. For example, benzotriazole and/or tolyltriazole have been crystallized from alcohols, benzene, cyclohexane, and xylenes. However, U.S. Pat. No. 3,637,514 and U.S. Pat. No. 3,732,239 (same inventors) teach that there are colored contaminants in the aryltriazoles which cannot be removed by crystallization of the free aryltriazole. Crystallization is also inherently a low yield process. Though aryltriazoles are poorly soluble in cold and ambient temperature water, they have some solubility in hot water. Unfortunately, the colored impurities share the same property.

Attempts to recrystallize free aryltriazoles from aqueous media typically precipitate the product with the colored impurities included. Generally, the aryltriazole separates as a melt, rather than a solid, and again, includes the colored impurities with it. The aryltriazole may be rendered soluble at ambient temperature by conversion to the aryltriazole anion with aqueous base. In this case, the colored impurities are also solubilized, generating a dark aqueous solution. Neutralization to a pH of about 5 or 6 regenerates the free aryltriazole, which precipitates as a solid or an oil. Without fail, the colored impurities are included in the precipitate, regenerating the discolored aryltriazole separated from a nearly colorless aqueous solution.

In the prior literature, aryl triazoles have been manipulated as the free aryltriazole under neutral conditions or as the aryltriazole anion under basic (alkaline) conditions. It has now been found that purification of aryltriazoles can be readily achieved by converting the aryltriazole to its cationic form under acidic conditions and separating the soluble aryltriazolium acid salt from the insoluble dark impurities by simple liquid/liquid phase separation.

SUMMARY OF INVENTION

I have found that contrary to the above cases of mutual solubility, aryltriazoles and their accompanying colored bodies exhibit differing solubilities in acidic aqueous media and that this property may be utilized to efficiently separate the two, thereby purifying the aryltriazole. In the preferred embodiment of this invention, the aryltriazole is fully solubilized by protonating the aryltriazole to its cationic salt with strong acid. Strong acids include the strong mineral acids, for example sulfuric acid, hydrochloric acid, nitric acid, phosphoric acid or perchloric acid. The colored impurities, whether protonated or not, remain insoluble in the acidic aqueous media and are removed as a separate liquid phase. The colored impurities may be removed in bulk without the disadvantages of using large quantities of decolorizing media, dangerous distillation techniques, or the handling of solids.

DESCRIPTION OF THE PREFERRED EMBODIMENT

In a preferred embodiment of this invention, as step 1, a sample of aryltriazole, black with colored impurities, is dissolved in 1 equivalent of hot 10 to 20% strong mineral acid to yield a biphasic liquid system. The (generally) upper layer consists of a solution of the aryltriazolium acid salt. The (generally) lower layer consists of essentially the colored impurities as a heavy black oil. As step 2, the two phases are separated. The aryltriazole acid salt layer may be drawn off or decanted. The color-body layer may also be drawn off conveniently as a liquid phase and sent to disposal, recycle or other manipulation. As step 3, aryltriazole acid salt layer is neutralized with base solution to release the free aryltriazole as a phase that is then separated from the aqueous components.

In step 1, it is preferable that at least 1 equivalent of strong mineral acid be used to solubilize the aryltriazole in its entirety. In the most preferred embodiment, the acid is sulfuric acid. As sulfuric acid is a diprotic acid, at least 0.5 moles of $H_2SO_4$ per 1.0 moles of aryltriazole is preferable. The diprotic sulfuric acid apparently is able to protonate and solubilize two individual aryltriazole molecules as the aryltriazole sulfate, though the solution may contain the aryltriazolium sulfate and/or the aryltriazolium bisulfate. The use of less than 1 equivalent of a strong acid generally leaves a portion of the aryltriazole unsolubilized with the loss of yield. In addition, it appears that under these conditions, the colored impurities continue to be entrained into the aqueous layer to some extent and discolor the aqueous layer. It is allowable to utilize more than 1 equivalent of strong acid to solubilize the aryltriazole without detrimental effect. For example 1.0 mole of aqueous $H_2SO_4$ per 1.0 mole of aryltriazole results in a decolorized aryltriazole sulfuric acid salt solution separated from a black colored impurities oil layer. In effect, 2 equivalents or stoicheometric $H_2SO_4$ have been used. The utilization of more than stoicheometric strong acid is not beneficial.

In step 2, the separation is preferably performed at elevated temperatures. I have found that while the aryltriazolium acid salts are readily soluble in aqueous solution at temperature above about 50° C. and completely soluble above about 80° C. to 100° C., the colored-bodies are not. In a closed vessel, temperatures may be above 100° C. with accompanying pressures above 1 atmosphere. In addition, the colored impurity layer is maintained in a more fluid state at elevated temperatures, making drawing-off or decantation easier. In the preferred embodiment of this invention, separation is performed preferably above 50° C., most preferably above 80° C.

According to step 3 of our invention, decolorized free aryl triazole may be recovered from the decolorized aryltriazole acid solution by neutralization with aqueous base. Suitable bases are aqueous solutions and slurries of NaOH, KOH, LiOH, $Ca(OH)_2$, $Mg(OH)_2$, $NaHCO_3$, $Na_2CO_3$, $KHCO_3$, $K_2CO_3$, $LiHCO_3$, $Li_2CO_3$, $NH_4OH$, etc. For example, titration with aqueous NaOH solution to a pH of 5 to 6 will precipitate decolorized free aryl triazole as a solid or a melt, depending on temperature. If desired, the free aryl triazole may be further treated with base to convert it to the anionic salt of the aryltriazole, i.e. sodium benzotriazole or sodium tolyltriazole. This may be performed as one step, treating the aryltriazole acid salt solution with enough base to neutralize the aryltriazolium acid salt plus another equivalent to deprotonate the free aryltriazole, or the process may be performed sequentially by first neutralizing the aryltriazolium acid salt and separating the free aryltriazole from the neutralized aqueous layer, then, in a second step, deprotonating the isolated free aryltriazole with aqueous base. The latter has the advantage of generating solutions of aryltriazole anion that are free of the salts of the parent strong acid and solutions that are more concentrated in aryltriazole anion.

It has been discovered further that in the process of our invention, the acidic aryltriazolium salt solution separated in step 2 may be purified further by precipitation of the solid aryltriazolium acid salt. The aryltriazole acid salts are poorly soluble at less than about 20° C. (room temperature) and very poorly soluble at temperatures less than about 0° C. By cooling the aryltriazolium acid solution separated in step 2 to room temperature or below, even further purified aryltriazolium acid salts precipitate. As such, in the case of sulfuric acid, a hot yellow solution of tolyltriazolium sulfuric acid salt upon cooling precipitates as snow white solid tolyltriazolium sulfuric acid salt which is filtered from the residual aqueous solution. The colored impurities remain dissolved in the residual aqueous solution. As the filter cake of the aryltriazolium salt tends to hold excess residual aqueous solution, it may be desired to recrystallize the aryltriazolium salt from hot water or hot aqueous acid, or simply rinse the cake with the cold water or cold aqueous acid. The further purified aryltriazole acid salt may then be submitted to step 3 of the process of the present invention for isolation of the free aryltriazole.

In a further embodiment of this invention, the residual aqueous solution from aryltriazolium acid salt precipitation may be recycled to the original acidification/separation step as it is a source of recyclable water and acid (pH remains 0 to 1). Further, upon recycle, many of the residual colored impurities are incorporated into the next colored impurities oil layer and, through saturation effects, are continuously removed with each recycle. For those colored impurities not removed by recycle, it has been found that passing the acidic residual aqueous solution through a bed of adsorbent media, such as carbon, effectively decolorizes and reconditions the mother liquor whereupon it may be recycled or disposed.

If desired, the acidic aryltriazolium acid solution separated in step 2 may be purified further by treatment with any of the applicable prior art methodologies. For example, the aryltriazolium acid salt solution may be passed through a bed of adsorbent media such as decolorizing carbon. This material has been found to reduce the color of such a solution from Gardner ~10 to Gardner 0.4. This is a vast improvement on the prior art as it has been found that much less carbon is necessary to effect the decolorization, the decolorization occurs at much faster flow rates, and the final color is much lighter than the direct decolorization methods. One adsorption media that we have discovered to be effective that is not in the prior art is the "oil only adsorbent media", commercially known a PIGs. In the form of sheets, pads or flock, "oil only adsorbents" are effective for removing residual colored impurity suspensions from the aryltriazolium acid solution. Conversely, we have found that "oil only adsorbents" are ineffective in decolorizing basic (alkaline) solutions of aryltriazole anions.

If desired, after isolating the free aryltriazole resulting from step 3 of this process, the aryltriazole may be subjected to further purification by any of the applicable prior art methodologies. For example the free aryltriazole may be recrystallized from any of the solvents listed above. The advantage here is that the feedstock for the crystallization has been already purified by the process of our invention and as such produces crystals and precipitates of improved purity. In addition, yields are higher as precipitation can be forced to a greater extent without the inclusion of colored impurities. The free aryltriazole may also be further purified by any of the distillation methods described in the prior art. The advantage here is that the feedstock for distillation has already been purified by the process of our invention and thus the entrainment of colored impurities is greatly reduced. Yields are improved and hazards nearly eliminated as the amount of still bottoms (as high energy colored impurities) has been reduced to negligible.

It has been discovered further that in the process of our invention, aryltriazolium acid salts may be used as a catalyst in the original synthetic reactions that generate aryltriazoles. There are also advantages in doing so. It has been shown in the literature that weak acids may be used advantageously as catalysts for the preparation of aryltriazoles from o-aryldiamines and nitrite salts. For example, acetic acid, citric acid, carbonic acid, glycolic acid, dihydrogen phosphate, oxalic acid, malonic acid, succinic acid, diglycolic acid, alkali metal bisulfates, alkanoic acids, benzoic acid and phthalic acid are disclosed as suitable weak acid catalysts. The free aryltriazole itself may be used as the acid catalyst and examples use about 6 mole percent. A disadvantage in using the free aryltriazole is that it must be introduced as a solid or freeze-prone melt. I have found that a portion of the aryltriazolium acid salt prepared by the process of our invention may be introduced to the original reaction of o-aryldiamines and nitrite salts as the weak acid catalyst with good effect. The biggest advantage is that the aryltriazolium acid salt may be conveniently introduced as an aqueous solution. Additionally the aryltriazolium sulfuric acid salt introduces two equivalents of acid for each mole of aryltriazole. This results in an approximately ⅓ reduction in the required mass of catalyst. As set forth in the specification herein, it is recognized from the above examples that a catalytically effective amount of weak acid is about 1 mole percent to about 10 mole percent weak acid. The weak acid is formally catalytic, that is it is neither consumed nor produced in the reaction. As such, the original nature of the reaction is not changed. For example, when the sodium salt of nitrous acid (sodium nitrite) is used as the nitration reagent, the sodium salt of the aryltriazole is produced. While it is typical to use the same aryltriazole acid salt as the aryltriazole to be produced by the reaction, there is nothing that precludes using a different aryltriazole salt to catalyze the reaction so long as mixed aryltriazoles are commercially acceptable in the final product. For example benzotriazolium sulfate may be used as catalyst for the reaction of o-toluenediamine with sodium nitrite to form tolyltriazole.

In this invention, it has been shown that crude, highly colored aryltriazoles may conveniently be purified by liquid/liquid separation of the colored impurities from the aryltriazoles. Central to the process of this invention is the treatment of the crude aryltriazole with an aqueous solution of a strong acid so as to completely solubilize the aryltriazole as its aryltriazolium acid salt. Strong acids include the mineral acids, sulfuric, phosphoric, nitric, perchloric and hydrochloric acid. These strong acids are by no means equivalent as their aryltriazolium acid salts vary in solubility and the acids themselves vary greatly in cost. Sulfuric acid is the least expensive and has good solubility characteristics. None-the-less, each acid bears potential usefulness within the scope of this invention.

Advantages of the present invention include the ability to purify aryltriazoles without the handling of solid reagents. The liquid/liquid process described allows the convenient and continuous pumping of liquid phases. A further advantage of the present invention is that impurities are separated and isolated at moderate temperatures that avoid risk of explosion or exothermic reaction. Such waste streams are also not rendered anhydrous, thus increasing their stability.

EXAMPLES

The following examples are for the purpose of illustration only and are not meant to limit the invention in any way.

Example 1

Isolation of Crude Tolyltriazole 500 g (1.58 mol) of crude 50% aqueous sodium tolyltriazole (black) was placed in a 2000 ml 3 necked flask. The solution was warmed to 60° C. with continuous stirring. The solution was titrated with 169.4 g (0.85 mol) of a solution of 50% aqueous $H_2SO_4$ to a pH of 5.25 and a temperature of 84° C. The mixture was transferred to a preheated separatory funnel and held in an 80° C. oven until complete separation had occurred. Upon draining, 261.5 g (1.55 mol) of a black oil was isolated that was 79% free tolyltriazole and 16% water Example 2

Liquid/Liquid Phase Separation of Dark Bodies from Tolyltriazole 13.3 g crude tolyltriazole oil (black) was stirred vigorously with 100 g of a hot solution of 10% $H_2SO_4$ in an erlenmeyer flask whereupon the majority of oil dissolved. The mixture was transferred to preheated separatory funnel and held in an 80° C. oven until complete separation had occurred. A small amount of black oil was observed as the bottom phase and adhering to the separatory funnel. The remaining upper phase was decanted off as a slightly yellow solution of the tolyltriazolium acid salt. This yellow solution had a Gardner color of 10.8.

The above experiment was repeated with only 90 g of 10% $H_2SO_4$. In this case, separation was incomplete and the upper layer was dark and oily.

The above experiment was repeated with 110 g of 10% $H_2SO_4$. In this case, separation was again complete and the upper layer was slightly yellow with a Gardner color of 10.8.

Example 3

Liquid/Liquid Phase Separation of Dark Bodies from Tolyltriazole 171.2 g crude tolyltriazole oil (black) was stirred vigorously with 980 g of a hot solution of 10% $H_2SO_4$ in an erlenmeyer flask whereupon the majority of oil dissolved. The mixture was transferred to preheated separatory funnel and held in an 80° C. oven until complete separation had occurred. Upon separation, 3.4 g of black oil was removed as the bottom phase while the remaining upper phase was a slightly yellow solution of acidified tolyltriazole. This yellow solution was quickly passed through a bed of 66 g decolorizing carbon to yield a final solution with a Gardner color of 0.5.

Example 4

Preparation and Precipitation of Tolyltriazole Hydrogensulfate Solution 66.5 g (0.5 mol) of 99% tolyltriazole flake was stirred vigorously with 490 g (0.5 mol) of a hot solution of 10% $H_2SO_4$ in an erlenmeyer flask whereupon the entirety dissolved to form a yellow solution. The mixture was allowed to cool overnight whereupon precipitation had occurred. The precipitate was vacuum filtered to yield 146.4 g of a white filter cake. The cake proved to be 44% by weight of water, inferring a 'dry' yield of 82 g. This corresponds to a 90% yield of (tolyltriazole)$_2$.H$_2$SO$_4$. The pH of the residual liquor was 0.2.

The above filter cake (0.225 mol) was suspended in 146 g H$_2$O and titrated with 73.2 g (0.458 mol) of 25% NaOH to a pH of 5.45. This corresponds to 101.6% of theoretical base for the neutralization of (tolyltriazole)$_2$.H$_2$SO$_4$.

Example 5

Preparation and Precipitation of Tolyltriazole Sulfate Solution 133 g (1.0 mol) of 99% tolyltriazole flake was stirred vigorously with 490 g (0.5 mol) of a hot solution of 10% $H_2SO_4$ in an erlenmeyer flask whereupon the entirety dissolved to form a yellow solution. The mixture was allowed to cool overnight whereupon precipitation had occurred. The precipitate was vacuum filtered to yield 262.2 g of a white filter cake. The cake proved to be 44% by weight of water, inferring a 'dry' yield of 147 g. This corresponds to an 80% yield of (tolyltriazole)$_2$.H$_2$SO$_4$. The pH of the residual liquor was 1.0.

22 g of the above wet filter cake (0.039 mol) was suspended in 11 g H$_2$O and titrated with 16 ml (0.032 mol) of 2M Na$_2$CO$_3$ to a pH of 5.27 at 55° C. This corresponds to 94% of theoretical base for the neutralization of (tolyltriazole)$_2$.H$_2$SO$_4$. The weight of isolated tolyltriazole was 8.47 g (0.064 mol) as a white solid. This corresponds to a 94% yield.

Example 6

Preparation and Precipitation of Benzotriazole Hydrogensulfate Solution 59.6 g (0.50 mol) of 98% benzotriazole flake was stirred vigorously with 245 g (0.50 mol) of a hot solution of 20% H$_2$SO$_4$ in an erlenmeyer flask whereupon the entirety dissolved to form a yellow solution. The mixture was allowed to cool several hours in an ice-water bath whereupon precipitation had occurred. The precipitate was vacuum filtered to yield a white filter cake. A second crop of precipitate was collected after further cooling of the mother liquor. The combine weight of solid product was 97.2 g. The filter cake proved to be 11.6% by weight of water, inferring a 'dry' yield of 85.8 g. This corresponds to a 102% yield of (benzotriazole)$_2$.H$_2$SO$_4$. The pH of the residual liquor was 0.2.

Example 7

Preparation and Precipitation of Benzotriazole Sulfate Solution 36.0 g (0.30 mol) of 98% benzotriazole flake was stirred vigorously with 73.5 g (0.15 mol) of a hot solution of 20% H$_2$SO$_4$ in an erlenmeyer flask whereupon the entirety dissolved to form a yellow solution. The mixture was allowed to cool several hours in an ice-water bath whereupon precipitation had occurred. The precipitate was vacuum filtered to yield a white filter cake. A second crop of precipitate was collected after further cooling of the mother liquor. The combine weight of solid product was 56.5 g. The filter cake proved to be 11.6% by weight of water, inferring a 'dry' yield of 50.0 g. This corresponds to a 98% yield of (benzotriazole)$_2$.H$_2$SO$_4$. The pH of the residual liquor was 0.1.

Example 8

Use of Benzotriazolium Sulfate as Catalyst for the Preparation of Benzotriazole from o-Diaminobenzene 108.0 g (1.0 mol) of o-diaminobenzene, 75.9 g (1.1 mol) NaNO$_2$, 205 g water and 10.0 g (0.03 mol) benzotriazolium sulfate were charged to a pressure reactor. The reaction was heated to 205° C. for 4 hours. The reactor was cooled to 50° C. and neutralized to pH 6 with 50% H$_2$SO$_4$. The contents were poured into a preheated separatory funnel and separated. The resulting oil was dried overnight at 150° C. to yield 117 g (98%) of benzotriazole.

I claim:

1. A process for purifying an impure aryltriazole obtained by the diazotization reaction of an ortho-phenylenediamine with a nitrite, said impure aryltriazole containing dark and colored impurities, consisting of the steps:
   1) dissolving at a temperature of 50 to 100° C. said impure aryltriazole with an aqueous solution of at least 1 equivalent of a 10-20% aqueous solution of strong acid to form two liquid phases, one phase of said two liquid phases comprising the cationic form of said aryltriazole in an aqueous solution and other phase of said two liquid phases comprising substantially all of the dark and colored impurities;

2) separating the one phase of the said two liquid phases comprising said cationic form of said aryltriazole in an aqueous solution from the other phase of the liquid mixture comprising substantially all of the dark and colored impurities;

3) neutralizing said one phase of the said two liquid phases comprising said cationic form of said aryltriazole in an aqueous solution with a base thereby forming two new phases, one phase being the purified impure aryltriazole and the other phase being a salt solution;

4) separating said purified impure aryltriazole from said salt solution.

2. A process for purifying impure tolyltriazole obtained by the diazotization reaction of an ortho-toluenediamine with a nitrite, said impure tolyltriazole containing dark and colored impurities, consisting of the steps:

1) dissolving at a temperature of 80 to 100° C. said impure tolyltriazole with an aqueous solution of at least 1 equivalent of a 10-20% aqueous solution of sulfuric acid to form two liquid phases, one phase of said two liquid phases comprising the cationic form of tolyltriazole in an aqueous solution and the other phase of said two liquid phases comprising substantially all of the dark and colored impurities;

2) separating the one phase of the said two liquid phases comprising said cationic form of tolyltriazole in an aqueous solution from the other phase of the liquid mixture comprising substantially all of the dark and colored impurities;

3) neutralizing said one phase of the said two liquid phases comprising said cationic form of tolyltriazole in an aqueous solution with sodium hydroxide solution thereby forming two new phases, one phase being the purified impure tolyltriazole and the other phase being a salt solution;

4) separating said purified impure tolyltriazole from said salt solution.

3. The process according to claim 1 wherein the impure aryltriazole is benzotriazole.

4. The process according to claim 1 wherein the impure aryltriazole is tolyltriazole.

5. The process according to claim 1 wherein the strong acid is selected from the group consisting of sulfuric acid, hydrochloric acid, nitric acid, phosphoric acid and perchloric acid.

6. The process according to claim 1 wherein the strong acid is sulfuric acid.

7. The process according to claim 1 wherein the strong acid is selected from the group consisting of phosphoric acid and nitric acid.

8. The process according to claim 1 wherein the base is selected from the group consisting of an alkali metal hydroxide, an alkaline earth metal hydroxide, an alkali metal carbonate, an alkaline earth metal carbonate, an alkali metal bicarbonate, ammonia, an amine and an alkali metal amide.

9. The process according to claim 1 wherein the base is sodium hydroxide.

10. The process according to claim 1 wherein the base is potassium hydroxide.

11. The process according to claim 1 wherein the base is sodium carbonate.

12. The process according to claim 1 wherein the base is sodium bicarbonate.

13. The process according to claim 1 wherein said dissolving is carried out using at least 1 equivalent of strong acid per mole of aryltriazole.

14. The process according to claim 1 wherein said dissolving is carried out using at least 0.5 moles (1 equivalent) of sulfuric acid per mole of aryltriazole.

15. The process according to claim 1 wherein said dissolving is carried out using at least 1.0 moles (1 equivalent) of strong acid selected from the group consisting of hydrochloric acid and nitric acid per mole of aryltriazole.

16. The process according to claim 1, step 2 wherein said separating is carried out at a temperature of from about 50 degrees centigrade to about 100 degrees centigrade (Celsius).

17. The process according to claim 1, step 2 wherein said separating is carried out at a temperature is from about 80 degrees centigrade to about 100 degrees centigrade (Celsius).

18. The process according to claim 8, whereas said purified impure aryltriazole is further treated with a base to form an aqueous solution containing the anionic form of said aryltriazole.

19. The process according to claim 1 wherein said salt solution of step 4 is recycled to form a recycle liquid, forming a solution of an impure aryltriazole with an 10-20% aqueous solution of a strong acid using said recycle liquid as the solvent, to form two liquid phases, one phase of said two liquid phases comprising the cationic form of said aryltriazole and the other phase of said two liquid phases comprising substantially all of the dark and colored impurities, and repeating steps 2, 3 and 4.

20. The process according to claim 1 wherein the aryltriazole is prepared by the reaction of an o-aryldiamine with a nitrite salt, and a catalytically effective amount of the cationic form of said aryltriazole a catalytically effective amount of an aryltriazole acid salt.

21. The improvement according to claim 20 wherein said aryltriazole acid salt is a benzotriazole acid salt.

22. The improvement according to claim 20 wherein said aryltriazole acid salt is a tolyltriazole acid salt.

23. The process according to claim 1 wherein the aqueous triazole acid salt solution of Step 2 is treated with an adsorbing media selected from the group consisting of activated carbon, kieselguhr, diatomaceous earth, clays, alumina, fuller's earth, pumice, sodium dithionite and "oil only" absorbents.

24. The process according to claim 1 wherein the aqueous triazole acid salt solution is treated with an adsorbing media consisting of "oil only" absorbents.

* * * * *